(12) United States Patent
Heo et al.

(10) Patent No.: US 6,724,474 B1
(45) Date of Patent: Apr. 20, 2004

(54) WAFER SURFACE INSPECTION METHOD

(75) Inventors: Tae-yeol Heo, Suwon (KR); Kyoo-chul Cho, Yongin (KR); Kyong-rim Kang, Seoul (KR); Soo-yeul Choi, Suwon (KR)

(73) Assignee: Samsung Electronics Co., Ltd., Suwon (KR)

( * ) Notice: Subject to any disclaimer, the term of this patent is extended or adjusted under 35 U.S.C. 154(b) by 157 days.

(21) Appl. No.: 09/670,817

(22) Filed: Sep. 28, 2000

(30) Foreign Application Priority Data

Sep. 30, 1999 (KR) .......................... 1999-42036

(51) Int. Cl.[7] ............................................ G01N 21/88
(52) U.S. Cl. ................................. 356/237.4; 356/237.5; 356/336; 356/337
(58) Field of Search .................................. 356/335, 336, 356/338, 343, 237.1, 237.2–237.5; 250/559.44

(56) References Cited

U.S. PATENT DOCUMENTS

| | | | |
|---|---|---|---|
| 5,667,584 A | * | 9/1997 | Takano et al. ............... 117/13 |
| 6,091,493 A | * | 7/2000 | Stover et al. ............... 356/336 |
| 6,118,525 A | * | 9/2000 | Fossey et al. ............ 356/237.2 |

FOREIGN PATENT DOCUMENTS

| | | |
|---|---|---|
| EP | 0 803 803 A2 | 10/1997 |
| WO | WO 98/25131 | 6/1998 |
| WO | WO 00/26646 | 5/2000 |

\* cited by examiner

Primary Examiner—Richard A. Rosenberger
Assistant Examiner—Vincent P. Barth
(74) Attorney, Agent, or Firm—Volentine Francos, PLLC (57) ABSTRACT

Types of defects on a wafer are discriminated according to defect measurements obtained from a wafer inspection system which includes a plurality of dark field detectors. Using the wafer measurement system, it is determined whether first, second and third conditions are satisfied. The first condition is when a size of a defect on the wafer measured by the wafer inspection system is smaller than a limit value denoting a maximum size of crystal originated particles. The second condition is when a correlation between a plurality of defect light intensity values detected by a plurality of dark field detectors of the wafer measurement system satisfies a reference value. The third condition is when a location of the defect measured by the wafer inspection system is within a vacancy-rich area of the wafer. The type of the defect is then determined to be a crystal originated particle when the first, second and third conditions are all satisfied. On the other hand, the type of defect is determined to be an actual particle when any one or more of the first, second and third conditions is not satisfied.

14 Claims, 5 Drawing Sheets

WAFER SURFACE INSPECTION METHOD

BACKGROUND OF THE INVENTION

1. Field of the Invention

The present invention relates to a method of inspecting a wafer surface. More particularly, the present invention relates to a method for discriminating among types of wafer defects using a wafer surface inspection device which detects multi-channel scattering light from a dark field or defect region of a wafer.

2. Description of the Related Art

Recently, the integration of integrated circuit (IC) memories has improved from 16 megabits to 64 megabits or more. As a result, pattern widths have taken on microscopic dimensions, and microscopic extraneous substances which did not cause problems in the past now act as sources of contamination and possible defects. Accordingly, when manufacturing highly integrated superhigh integration LSI devices such as 64 megabit-dynamic random access memories (DRAMs) or 256 megabit-DRAMs, it is desirable to thoroughly control and thus avoid defects and/or micro-sized extraneous substances on the wafer to thereby significantly enhance yield.

Generally, the size of a defect which can cause problems is a factor of the minimum wiring width of the superhigh integration LSI to be manufactured. For example, it is necessary to control micro-sized defects which have diameters of 0.1–0.2 $\mu$m or less in 256 megabit-DRAMs or in devices having capacities more than the 256 megabit-DRAMs, which are implemented according to a design rule of 0.23 $\mu$m or less.

Defects which cause problems during the manufacture of superhigh integration LSI devices can be largely divided into two types. One is "crystal originated particle" (COP) defects formed on a wafer surface or inside the wafer during manufacture of the wafer. The other is actual dust or contaminants (hereinafter, called particles) adhering to the wafer surface.

COPs are generated during the manufacture of silicon wafers. Generally, crystal defects called "as-grown" defects are introduced in an ingot of single crystal silicon which is pulled according to a so-called Czochralski method (hereinafter, called a CZ method) during the growth of the single crystal silicon. This crystal defect is not removed during crystal cooling and remains in the processed and manufactured wafer. In this state, when wet-cleaning is performed (which is generally used to remove particles adhering to the surface of the wafer), micro pits are formed on the wafer surface since the etching rate is greater at or in the vicinity of the crystal defects on the wafer than at portions of the wafer which are free of such defects. Here, such pits are called COPs.

Figure 1:
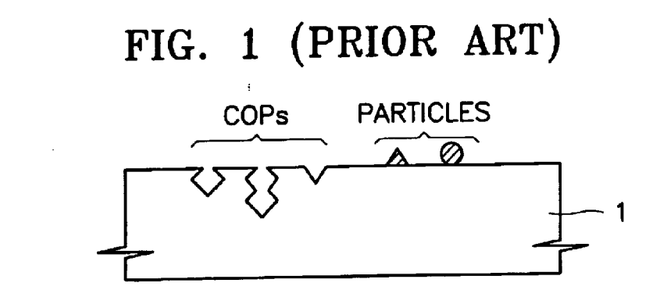
FIG. 1 is a sectional view showing representations of Crystal Originated Particles (COPs) and actual particles appearing in a wafer.

FIG. 1 is a sectional view showing representations of COPs and particles on a wafer 1. It is known that the COP degrades the electric breakdown characteristic of a gate oxide film on a semiconductor device. Furthermore, the COP acts as a contamination source on the wafer which can cause breaking or shortcircuiting of a circuit pattern. As such, the COP may result in defective products or decreased product quality and reliability.

When a wafer having both COPs and particles is measured by a conventional particle counter or a wafer inspection device, frequently the COPs (which are vacancy-type defects) are mistakenly detected as particles. That is, the COPs are not accurately discriminated from particles which correspond to actual contaminants. However, to properly manage defects and thus improve yield, it is important to accurately discriminate COPs from particles on a wafer. Therefore, it is desirable to quantitatively measure and analyze the states of the COPs and/or the particles on the wafer to permit discrimination thereof.

U.S. Pat. No. 5,640,238, issued to Nakano et al., discloses a conventional technology for discriminating COPs from particles on a wafer. In this patent, a method of inspecting particles comprises the steps of: making a first particle map by particle measurement on a wafer to be inspected; performing a particle removing treatment to remove particles from the wafer; making a second particle map by particle measurement on the wafer which was subjected to the particle removing treatment; and comparing the first particle map with the second particle map. Particles appearing at each immobile point common in both the first and second particle maps are determined to be crystal defects or surface irregularities, and particles appearing in the first particle map but not in the second particle map are determined to be real dust particles or contaminants.

In such conventional technology, however, since a cleaning process must be carried out to remove particles from a wafer, there is a disadvantage in that it takes additional time to monitor the particles on the wafer. Particularly, since the process for removing particles must be carried out even when only COPs which affect yield are present (as opposed to particles which may be dealt with during fabrication), an unnecessary process is redundantly added, thereby increasing processing time. Moreover, when using a wet-cleaning process to remove particles according to the conventional technology, not only do cleaning solutions cause environmental pollution, but the COPs become larger due to an etching effect of the wet-cleaning process. Further, the conventional technology cannot be applied to achieve in-situ monitoring during the manufacture of devices, and the wafers used for the monitoring cannot be reused, thereby decreasing productivity.

SUMMARY OF THE INVENTION

It is an object of the present invention to provide a method of inspecting a wafer surface which allows in-situ monitoring during the manufacture of semiconductor devices and which rapidly and accurately discriminates COPs from actual particles on the wafer.

To achieve the object of the present invention, there is provided a wafer surface inspection method for discriminating among types of defects on a wafer according to defect measurements obtained from a wafer inspection system which includes a plurality of dark field detectors. Using the wafer measurement system, it is determined whether first, second and third conditions are satisfied. The first condition is when a size of a defect on the wafer measured by the wafer inspection system is smaller than a limit value denoting a maximum size of crystal originated particles. The second condition is when a correlation between a plurality of defect light intensity values detected by a plurality of dark field detectors of the wafer measurement system satisfies a reference condition. The third condition is when a location of the defect measured by the wafer inspection system is within a vacancy-rich area of the wafer. The type of the defect is then determined to be a crystal originated particle when the first, second and third conditions are all satisfied. On the other hand, the type of defect is determined to be an actual particle when any one or more of the first, second and third conditions is not satisfied. Preferably, the limit value indicating a maximum size of COPs is 0.16 μm, and the wafer inspection system is a scatterometric particle measurement system.

Each of the dark field detectors may include a wide angle photo-multiplier tube for detecting light scattered from the defect at a wide angle and a narrow angle photo-multiplier tube for detecting light scattered from the defect at a narrow angle. In this case, the plurality of defect light intensity values include a defect intensity value $S_W$ obtained from the wide angle photo-multiplier tube and a defect intensity value $S_N$ obtained from the narrow angle photo-multiplier tube, and the second condition is where an intensity ratio $S_N/S_W$ of the intensity value $S_N$ to the intensity value $S_W$ exceeds the reference value.

Alternately, each of the dark field detectors may include a small angle detector for detecting light components scattered forward from the defect at a small angle, a medium angle detector for detecting light components scattered perpendicularly from the defect at a medium angle and a large angle detector for detecting light components scattered backwardly from the defect at a large angle. In this case, the plurality of defect light intensity values include a defect light intensity value $S_S$ obtained from the small angle detector, a defect light intensity value $S_M$ obtained from the medium angle detector and a defect light intensity value $S_L$ obtained from the large angle detector, and the second condition is where both (a) an intensity ratio $S_M/S_L$ of the intensity value $S_M$ to the intensity value $S_L$ exceeds a first reference value and (b) an intensity ratio $S_M/S_S$ of the intensity value $S_M$ to the intensity value $S_S$ exceeds a second reference value.

According to the present invention, the error rate of the defect discrimination is minimized, inspection of the wafer surface may be achieved by in-situ monitoring during the manufacture of semiconductor devices, and the type of defect on the wafer is rapidly and accurately determined in a nondestructive manner.

BRIEF DESCRIPTION OF THE DRAWINGS

The above object and advantages of the present invention will become more apparent by describing in detail a preferred embodiment thereof with reference to the attached drawings in which.

DETAILED DESCRIPTION OF THE INVENTION

Defects on a wafer are typically measured with a scatterometric particle measurement system. Known systems of this type include a Surfscan SP1 TBI (manufactured by KIa-Tencor Corporation in the U.S.A.) and an Advanced Wafer Inspection System (AWIS) (manufactured by ADE Optical Systems Corporation in the U.S.A.). Each of these systems is used to discriminate between actual particles and crystal originated particles (COPs) on a wafer.

Figure 2A:
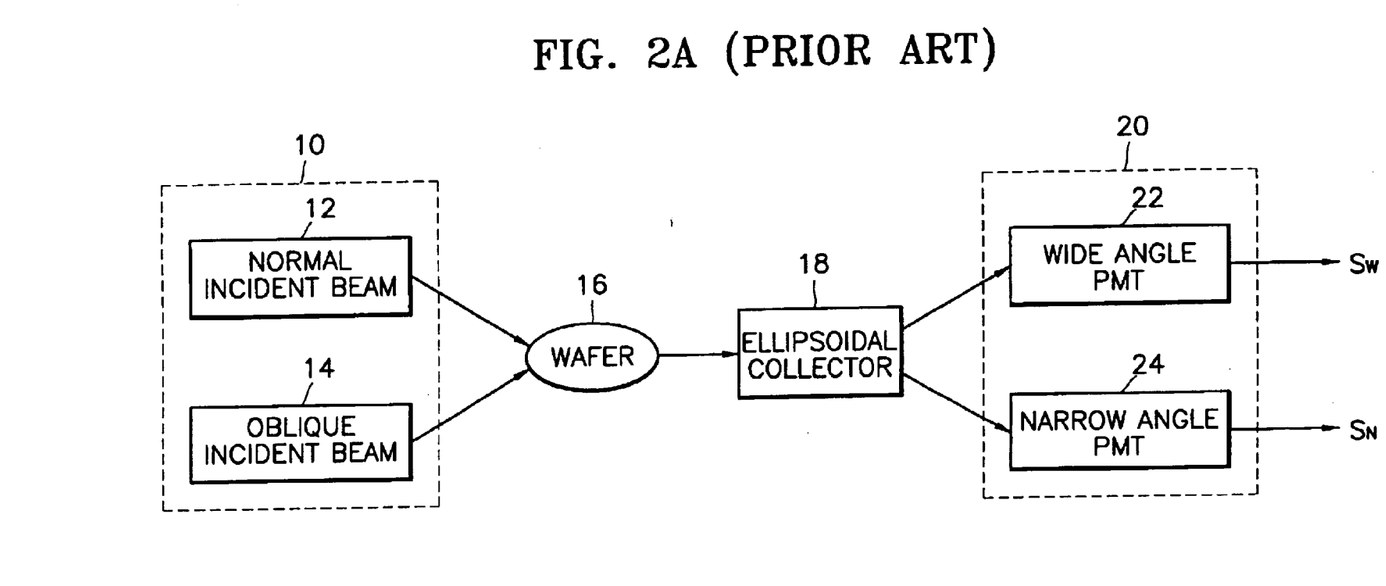
FIG. 2A is a block diagram schematically showing part of an optical system which inspects a dark field of a wafer in an example of a conventional inspection system.

FIG. 2A is a block diagram schematically showing part of an optical system which inspects dark fields of a wafer in the Surfscan SP1 TBI inspection system. Dark fields are optical anomalies that have been detected on regions of the wafer and denote suspected defects of one kind or another, i.e., COPs or actual particles. Referring to FIG. 2A, a normal incident beam 12 and an oblique incident beam 14 are used as light sources of a dark field illumination 10. The normal incident beam 12 and the oblique incident beam 14 are radiated onto a dark field of a wafer 16. Light scattered from the dark field is reflected by an ellipsoidal collector 18 and then detected by a dark field detector 20. The dark field detector 20 comprises a wide angle photo-multiplier tube (PMT) 22 for detecting scattering light in a relatively wide angle range and a narrow angle PMT 24 for detecting scattering light in a relatively narrow angle range.

The angular range of the scattering light reflected from a defect on the wafer 16 varies with a type of the defect of the dark field. For example, an angle of scattering light reflected from a COP which is a pit type crystal defect is narrower than an angle of scattering light reflected from an actual particle adhering to and protruding from the surface of the wafer 16.

The wide angle PMT 22 and the narrow angle PMT 24 generate different image data $S_W$ and $S_N$, respectively, according to the intensity of the detected scattering light, such data varying with the type of defect within the dark field on the wafer 16. The Surfscan SP1 TBI inspection system identifies whether the dark field (defect) on the wafer is a COP or an actual particle by subjecting the values $S_W$ and $S_N$ obtained from the wide angle PMT 22 and the narrow angle PMT 24 to a defect discrimination algorithm.

Figure 2B:
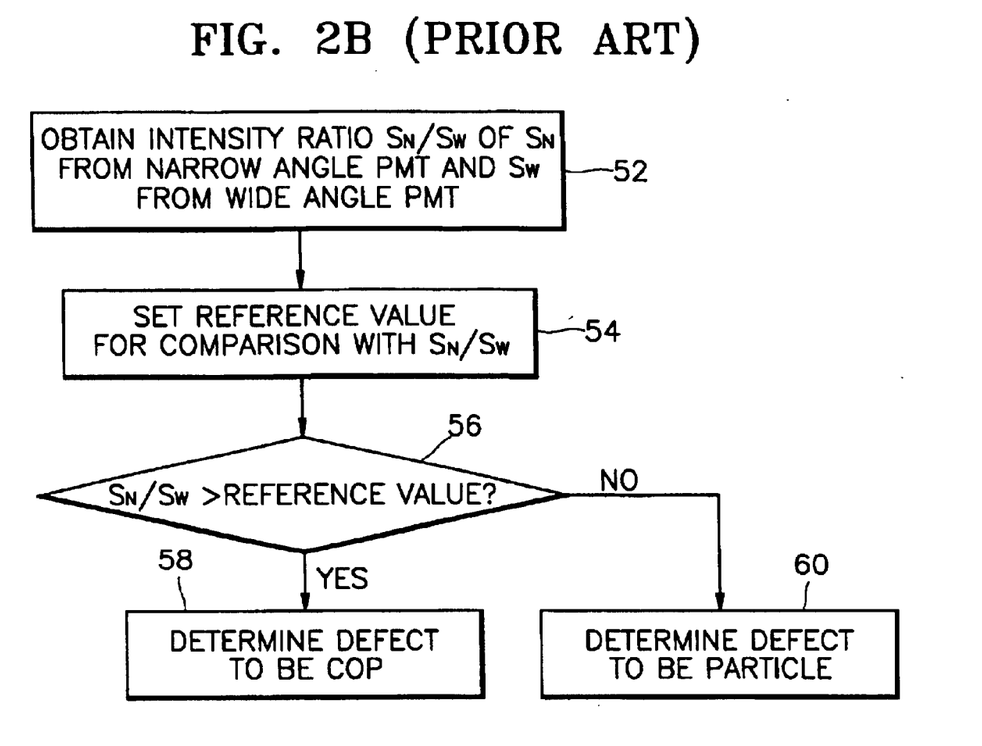
FIG. 2B is a flowchart showing a defect discrimination algorithm adopted in the inspection system of FIG. 2A.

FIG. 2B is a flowchart for explaining the defect discrimination algorithm used in the Surfscan SP1 TBI inspection system which adopts the optical system of FIG. 2A. Referring to FIG. 2B, after obtaining the defect intensity values $S_W$ and $S_N$ from the wide angle PMT 22 and the narrow angle PMT 24, the intensity ratio $S_N/S_W$ of the defect size value $S_N$ to the defect intensity value $S_W$ is obtained in step 52. A predetermined reference value (for example, 1.2) for comparison with the intensity ratio $S_N/S_W$ is set in step 54. The intensity ratio $S_N/S_W$ is then compared with the reference value in step 56. When the value of $S_N/S_W$ exceeds the reference value, it is determined that a defect detected in the wafer is a COP in step 58. When the value of $S_N/S_W$ does not exceed the reference value, it is determined that the detected defect is an actual particle in step 60.

Figure 3A:
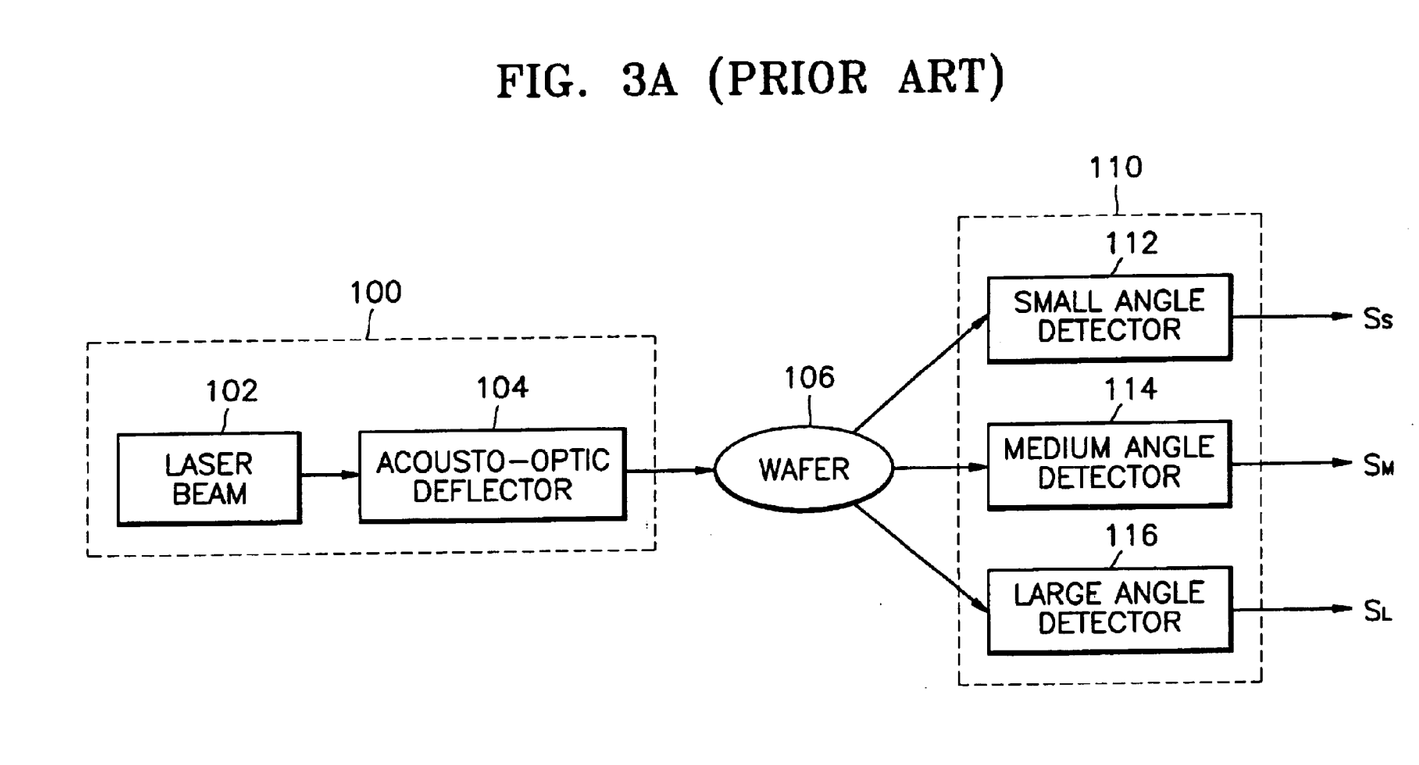
FIG. 3A is a block diagram schematically showing part of an optical system which inspects a dark field of a wafer in another example of a conventional inspection system.

FIG. 3A is a block diagram schematically showing part of an optical system which inspects a dark field of a wafer in the AWIS mentioned above. Referring to FIG. 3A, a laser beam 102 radiated from the laser of a scanner 100 scans the surface of a wafer 106 via an acousto-optic deflector 104, and scattering light reflected from the surface of the wafer 106 is detected by a dark field detector 110.

The dark field detector 110 comprises a small angle detector 112, a medium angle detector 114 and a large angle detector 116. Light components scattered forwardly from a defect of the surface of the wafer 106 are collected in a relatively small angle range by a small angle collector (not shown) and detected by the small angle detector 112. Light components scattered perpendicularly from the defect of the surface of the wafer 106 are collected in a relatively medium angle range by a medium angle collector (not shown) and detected by the medium angle detector 114. Light components scattered backwardly from the defect of the surface of the wafer 106 are collected in a relatively large angle range by a large angle collector (not shown) and detected by the large angle detector 116. The small angle detector 112, the medium angle detector 114 and the large angle detector 116 then generate defect intensity values $S_S$, $S_M$ and $S_L$ (image data) from the detected light intensities, respectively.

Measurement principles used in the inspection system having the configuration shown in FIG. 3A, or the configuration of an apparatus for embodying such principles, is disclosed in detail in U.S. Pat. No. 5,712,701, issued to Clementi et al. The AWIS determines whether the type of defect on the wafer is a COP or a particle by subjecting the defect intensity values $S_S$, $S_M$ and $S_L$ obtained from the small angle detector 112, the medium angle detector 114 and the large angle detector 116, respectively, to a defect discrimination algorithm.

Figure 3B:
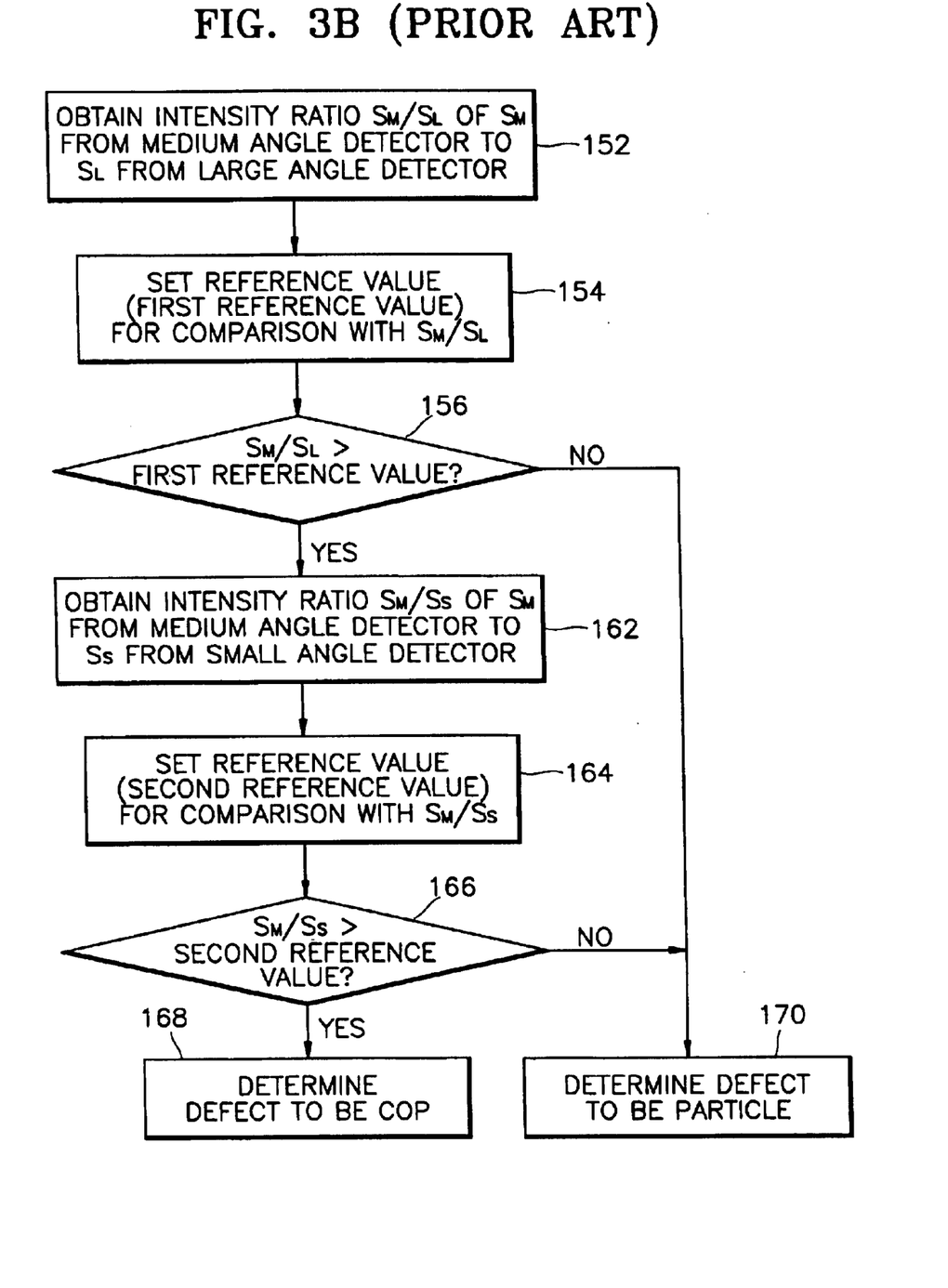
FIG. 3B is a flowchart showing a defect discrimination algorithm adopted in the inspection system of FIG. 3A.

FIG. 3B is a flowchart showing the defect discrimination algorithm used in the AWIS which adopts the optical system of FIG. 3A. Referring to FIG. 3B, the defect intensity values $S_S$, $S_M$ and $S_L$ are obtained from the small angle detector 112, the medium angle detector 114 and the large angle detector 116 as in FIG. 3A, and then an intensity ratio $S_M/S_L$ of the defect size value $S_M$ to the defect intensity value $S_L$ is obtained in step 152. A predetermined reference value (for example, 1.0) is set as a first reference value for comparison with the intensity ratio $S_M/S_L$ in step 154. Thereafter, the intensity ratio $S_M/S_L$ is compared with the first reference value in step 156. When the value of $S_M/S_L$ does not exceed the first reference value, the defect is determined to be an actual particle in step 170. When the value of $S_M/S_L$ exceeds the first reference value in the step 156, an intensity ratio $S_M/S_S$ of the defect size value $S_M$ to the defect size value $S_S$ is obtained in step 162. A predetermined reference value (for example, 1.25) is set as a second reference value for comparison with the intensity ratio $S_M/S_S$ in step 164. Thereafter, the intensity ratio $S_M/S_S$ is compared with the second reference value in step 166. When the value of $S_M/S_S$ does not exceed the second reference value, the defect is determined to be an actual particle in the step 170. When the value of $S_M/S_S$ exceeds the second reference value in the step 166, the defect detected from the wafer is determined to be a COP in step 168.

The above-described inspection systems, which discriminate between COPs and particles on a wafer in accordance with such defect discrimination algorithms as shown in FIGS. 2B and 3B, have relatively high error rates, particularly when discriminating micro defects having dimensions of less than 0.2 μm. That is, at these dimensions, COPs are frequently detected as actual particles.

Specifically, when inspecting the surface of a wafer and measuring sizes of detected defects using the inspection systems described above, it is found that defects determined to be COPs substantially have sizes between 0.12–0.16 μm and that defects determined as particles substantially have sizes greater than or equal to 0.16 μm. Moreover, according to the defect discrimination algorithms of the inspection systems as described above, only COPs or particles having sizes greater than or equal to 0.16 μm can be discriminated.

However, using an atomic force microscope (AFM), it was confirmed that most COPs substantially have sizes smaller than 0.16 μm. In addition, when the sizes of defects determined to be COPs according to the defect discrimination algorithms in the above-described inspection systems are detected as being greater than or equal to 0.16 μm, it turned out (by AFM testing) that the defects were substantially not COPs but instead were actual particles.

During wafer manufacture employing the CZ method, due to the thermal behavior of point defects caused by the difference in heat distribution at the boundary between molten silicon and single crystal silicon occurring when growing single crystal silicon from the molten silicon, crystal lattice vacancies causing crystal defects such as COPs mainly appear at the center area of the wafer. An area at a predetermined distance from the center of the wafer forms an interstitial rich area (hereinafter, called an I-rich area) having only defects caused by interstitial atoms. For the center area of the wafer in which the COPs may appear, namely, a vacancy-rich area (hereinafter, called a V-rich area), the range of the V-rich area is predetermined according to the type of wafer during the manufacture of the wafer and is adjustable. The range of the V-rich area of a wafer of a certain type is the same as that of another wafer of the same type.

However, according to the defect discrimination algorithms adopted in wafer inspection methods using the inspection systems described above, defects detected in the I-rich area are sometimes determined to be COPs. When the defects detected in the I-rich area are determined to be COPs in accordance with the defect discrimination algorithms of the inspection systems, such results of the discrimination are all errors. This judgement is also supported by test results confirmed using an AFM.

Accordingly, to improve yield during manufacture of superhigh integration LSI devices requiring thorough management on extraneous substances having diameters of 0.1–0.2 μm or less, it is necessary to develop a new algorithm for accurately determining whether defects on a wafer are COPs or particles taking into account the causes of errors which may occur in the inspection discrimination algorithms used in such existing wafer inspection systems as described above, thereby minimizing error rates.

Figure 4:
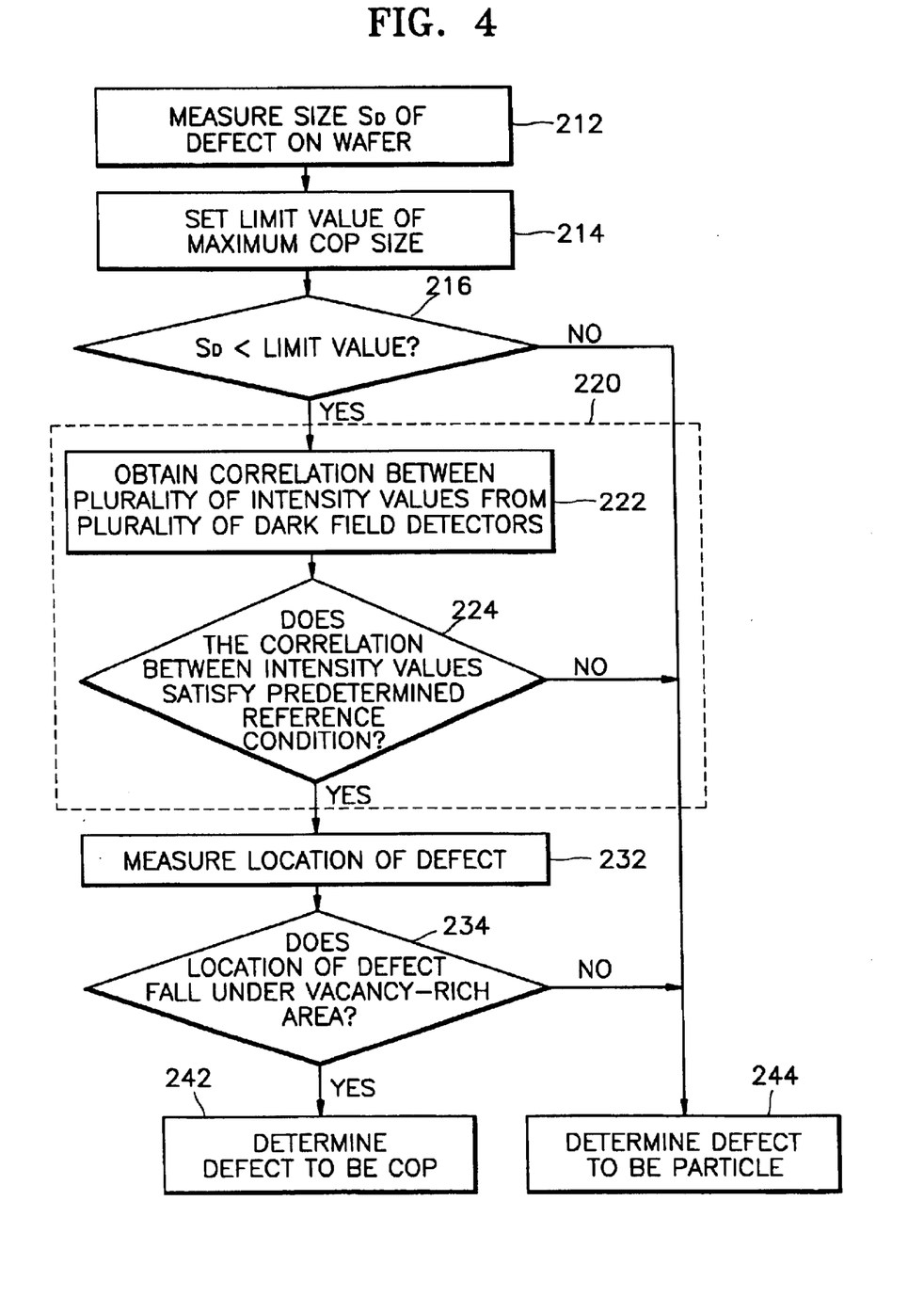
FIG. 4 is a flowchart showing a defect discrimination algorithm adopted in a wafer surface inspection method according to a preferred embodiment of the present invention.

FIG. 4 is a flowchart showing a defect discrimination algorithm adopted in a wafer surface inspection method according to a preferred embodiment of the present invention. The defect discrimination algorithm described in FIG. 4 can be applied to the existing wafer inspection systems described above.

Referring to FIG. 4, a size $S_D$ of a defect on a wafer is first measured using a wafer inspection system (such at those described above) in step 212. A limit value of a maximum size of COPs appearing on the wafer is set in step 214. Here, according to the results of inspection using an AFM, it was demonstrated that the maximum size of COPs on a wafer is about 0.16 μm and that defects greater than 0.16 μm were particles. Accordingly, in the embodiment of the present invention, the limit value of the maximum size of COPs is set to 0.16 μm in the step 214.

Subsequently, the measured defect size $S_D$ is compared with the limit value in step 216. When the measured defect size $S_D$ is greater than or equal to the limit value, namely, 0.16 μm in the step 216, the defect is determined to be a particle in step 244. When the measured defect size $S_D$ is smaller than the limit value 0.16 μm in the step 216, it is determined that subsequent discrimination steps are needed.

When the measured defect size $S_D$ is smaller than the limit value 0.16 μm, the defect is further discriminated based on a correlation between a plurality of intensity values obtained from a plurality of dark field detectors provided in the wafer inspection system in step 220. A predetermined correlation between the plurality of intensity values is obtained in step 222, and then it is determined whether the correlation between the intensity values satisfies a predetermined reference condition in step 224. According to a result of this determination, the type of defect is discriminated. That is, if the correlation between the intensity values does not satisfy the predetermined reference condition, the defect is discriminated as a particle. On the other hand, if the reference condition is satisfied, then further discrimination of the defect is needed.

The correlation and predetermined reference condition of step 220 may be adopted and analyzed in the same manner as described above in connection with the algorithms of FIG. 2B or FIG. 3B.

For example, in the case of adopting the algorithm of FIG. 2B, defect intensity values $S_W$ and $S_N$ are obtained from the wide angle PMT 22 and the narrow angle PMT 24, respectively. Thereafter, as the correlation between these defect intensity values, an intensit ratio $S_N/S_W$ is obtained in the step 222. A predetermined reference value (for example, 1.2), which is set in the same manner as that described in the step 54 of FIG. 2B, is then compared with the intensity ratio $S_N/S_W$. It is then determined whether the reference condition of $S_N/S_W > 1.2$ is satisfied in the step 224.

When the correlation represented as the intensity ratio $S_N/S_W$ does not satisfy the condition in the step 224, the defect is determined to be a particle in the step 244. When the correlation satisfies the reference condition in the step 224, it is determined that subsequent defect discrimination is needed.

When instead adopting the algorithm of FIG. 3B as step 220, defect intensity values $S_S$, $S_M$ and $S_L$ are obtained from the small angle detector 112, the medium angle detector 114 and the large angle detector 116, respectively. Thereafter, in step 222, as a first correlation between the defect intensity values, an intensity ratio $S_M/S_L$ is obtained in the same manner as in the step 152 of FIG. 3B and, as a second correlation between the defect intensity values, an intensity ratio $S_M/S_S$ is obtained in the same manner as in the step 162 of FIG. 3B.

Subsequently, to determine whether the first and second correlations satisfy predetermined reference conditions, the same methods as in the steps 156 and 166 of FIG. 3B are adopted, with the exception that the first and second reference values are set at 1.14 in the present embodiment in the step 224. A first reference condition is predetermined as $S_M/S_L > 1.14$. Then, it is determined whether the first reference condition is satisfied, that is, whether the first correlation exceeds the first reference value. In addition, a second reference condition is predetermined as $S_M/S_S > 1.14$. Then, it is determined whether the second reference condition is satisfied, that is, whether the second correlation exceeds the second reference value. The predetermined first and second reference values can be changed according to process conditions or installation conditions.

When either the first reference condition or the second reference condition is not satisfied, the defect is determined to be a particle in the step 244. When the first and second reference conditions are both satisfied, it is determined that subsequent defect discrimination steps are needed.

When the condition(s) are all satisfied in the step 224, the location of the defect is measured using the wafer inspection system in step 232. Thereafter, it is determined whether the location of the defect falls under the V-rich area or the I-rich area on the wafer in step 234. For example, in the case of a wafer having an I-rich area extending from the edge of the wafer to a radius of 50 mm and a V-rich area in the remaining central part of the wafer, it is determined whether the location of the defect is outside the range between the edge of the wafer to the radius of 50 mm in the step 234.

When the location of the defect is not within the V-rich area on the wafer in the step 234, the defect is determined to be a particle in the step 244. When the location of the defect is within the V-rich area on the wafer, the defect is determined to be a COP in step 242.

In addition to the discrimination conditions adopted in the defect discrimination algorithms of existing wafer inspection systems, the wafer surface inspection method according to the present invention uses an algorithm which further determines whether the size of a defect is smaller than a limit value representing the maximum size of COPs and which further determines whether the defect appears in the V-rich area on a wafer, thereby more accurately discriminating the type of defect on the wafer. Therefore, the case in which a defect having a size greater than a maximum size of COPs is discriminated as a COP and the case in which a defect in the I-rich area is discriminated as a COP are prevented, thereby minimizing an error rate during the overall discrimination process.

Furthermore, the defect discrimination algorithm according to the wafer inspection method of the present invention can be applied to existing inspection systems. Combining the inspection system with a cluster tool allows a wafer surface to be inspected by in-situ monitoring during manufacture of semiconductor devices. The present invention also accurately and rapidly determines the type of defect on a wafer using a nondestructive method, thereby improving productivity.

Although the present invention has been described with reference to particular embodiments, it will be apparent to one of ordinary skill in the art that modification of the described embodiments may be made without departing from the spirit and scope of the invention. As one example only, one of ordinary skill will readily appreciate that the order of the process steps appearing in FIG. 4 may be rearranged. That is, the size discrimination (steps 212–216), the light intensity discrimination (step 220), and the location discrimination (steps 232–234) may be carried out in any order.

What is claimed is:

1. A wafer surface inspection method for discriminating among types of defects on a wafer according to defect measurements obtained from a wafer inspection system which includes a plurality of dark field detectors, said method comprising:

determining whether a first condition is satisfied in which a size of a defect on the wafer measured by the wafer inspection system is smaller than a limit value denoting a maximum size of crystal originated particles;

determining whether a second condition is satisfied in which a correlation between a plurality of defect light intensity values detected by the plurality of dark field detectors satisfies a reference value;

determining whether a third condition is satisfied in which a location of the defect measured by the wafer inspection system is within a vacancy-rich area of the wafer; and determining that the type of the defect is a crystal originated particle when the first, second and third conditions are all satisfied, and determining that the type of defect is an actual particle when any one or more of the first, second and third conditions is not satisfied.

2. The wafer surface inspection method of claim 1, wherein the limit value is 0.16 μm.

3. The wafer surface inspection method of claim 1, wherein a scatterometric particle measurement system is used as the wafer inspection system.

4. The wafer surface inspection method of claim 3, wherein each of the dark field detectors comprises a wide angle photo-multiplier tube for detecting light scattered from the defect at a wide angle and a narrow angle photo-multiplier tube for detecting light scattered from the defect at a narrow angle.

5. The wafer surface inspection method of claim 4, wherein the plurality of defect light intensity values include a defect intensity value $S_W$ obtained from the wide angle photo-multiplier tube and a defect intensity value $S_N$ obtained from the narrow angle photo-multiplier tube, and wherein the second condition is where an intensity ratio $S_N/S_W$ of the intensity value $S_N$ to the intensity value $S_W$ exceeds the reference value.

6. The wafer surface inspection method of claim 3, wherein each of the dark field detectors comprises a small angle detector for detecting light components scattered forward from the defect at a small angle, a medium angle detector for detecting light components scattered perpendicularly from the defect at a medium angle and a large angle detector for detecting light components scattered backwardly from the defect at a large angle.

7. The wafer surface inspection method of claim 6, wherein the plurality of defect light intensity values include a defect light intensity value $S_S$ obtained from the small angle detector, a defect light intensity value $S_M$ obtained from the medium angle detector and a defect light intensity value $S_L$ obtained from the large angle detector, and wherein the second condition is where both (a) an intensity ratio $S_M/S_L$ of the intensity value $S_M$ to the intensity value $S_L$ exceeds a first reference value and (b) an intensity ratio $S_M/S_S$ of the intensity value $S_M$ to the intensity value $S_S$ exceeds a second reference value.

8. A wafer surface inspection method for discriminating among types of defects on a wafer, said method comprising:

using a wafer inspection system to measure a size of a defect on the wafer;

determining whether a first condition is satisfied in which a size of the defect on the wafer is smaller than a limit value denoting a maximum size of crystal originated particles;

using a plurality of dark field detectors of the wafer inspection system to respectively detect a plurality of defect light intensity values of the defect;

determining whether a second condition is satisfied in which a correlation between the plurality of defect light intensity values satisfies a reference value;

using the wafer inspection system to determine a location of the defect;

determining whether a third condition is satisfied in which the location of the defect is within a vacancy-rich area of the wafer; and determining that the type of the defect is a crystal originated particle when the first, second and third conditions are all satisfied, and determining that the type of defect is an actual particle when any one or more of the first, second and third conditions is not satisfied.

9. The wafer surface inspection method of claim 8, wherein the limit value is 0.16 μm.

10. The wafer surface inspection method of claim 8, wherein a scatterometric particle measurement system is used as the wafer inspection system.

11. The wafer surface inspection method of claim 10, wherein each of the dark field detectors comprises a wide angle photo-multiplier tube for detecting light scattered from the defect at a wide angle and a narrow angle photo-multiplier tube for detecting light scattered from the defect at a narrow angle.

12. The wafer surface inspection method of claim 11, wherein the plurality of defect light intensity values include a defect intensity value $S_W$ obtained from the wide angle photo-multiplier tube and a defect intensity value $S_N$ obtained from the narrow angle photo-multiplier tube, and wherein the second condition is where an intensity ratio $S_N/S_W$ of the intensity value $S_N$ to the intensity value $S_W$ exceeds the reference value.

13. The wafer surface inspection method of claim 10, wherein each of the dark field detectors comprises a small angle detector for detecting light components scattered forward from the defect at a small angle, a medium angle detector for detecting light components scattered perpendicularly from the defect at a medium angle and a large angle detector for detecting light components scattered backwardly from the defect at a large angle.

14. The wafer surface inspection method of claim 13, wherein the plurality of defect light intensity values include a defect light intensity value $S_S$ obtained from the small angle detector, a defect light intensity value $S_M$ obtained from the medium angle detector and a defect light intensity value $S_L$ obtained from the large angle detector, and wherein the second condition is where both (a) an intensity ratio $S_M/S_L$ of the intensity value $S_M$ to the intensity value $S_L$ exceeds a first reference value and (b) an intensity ratio $S_M/S_S$ of the intensity value $S_M$ to the intensity value $S_S$ exceeds a second reference value.

* * * * *